United States Patent [19]
Hamann et al.

[11] Patent Number: 5,223,390
[45] Date of Patent: Jun. 29, 1993

[54] ANALYTICAL ELEMENTS CONTAINING NON-REACTIVE BLOCKING DYES

[75] Inventors: John E. Hamann, Spencerport; Merrit N. Jacobs, Fairport; Daniel A. Nealon; Charles H. Appell, both of Rochester; Richard L. Detwiler, Webster, all of N.Y.

[73] Assignee: Eastman Kodak Company, Rochester, N.Y.

[21] Appl. No.: 617,319

[22] Filed: Nov. 23, 1990

[51] Int. Cl.$^5$ .............. C12Q 1/00; C12Q 1/48; G01N 21/77
[52] U.S. Cl. .......................... 435/4; 435/15; 435/26; 436/170; 552/208
[58] Field of Search .............. 435/4, 15, 26; 436/170; 422/82.05; 552/208

[56] References Cited

U.S. PATENT DOCUMENTS 4,877,721 10/1989 Diehl .................................. 430/522
5,066,462 11/1991 Kawasaki .............................. 422/56

FOREIGN PATENT DOCUMENTS 0229982 7/1987 European Pat. Off. .

*Primary Examiner*—Michael G. Wityshyn
*Assistant Examiner*—Ralph Gitomer
*Attorney, Agent, or Firm*—John R. Everett

[57] ABSTRACT

An analytical element for quantitatively assaying an analyte by measuring reflection density in the range 320 to 360 nm. The element comprises a reagent layer and a registration layer. One of such layers contains a dye which has a low absorbtivity band from 320 to 360 nm and a high absorbtivity band from 640 to 720 nm.

6 Claims, 2 Drawing Sheets

ANALYTICAL ELEMENTS CONTAINING NON-REACTIVE BLOCKING DYES

FIELD OF THE INVENTION

This invention relates to the field of clinical chemistry. More specifically, it relates to analytical elements for quantitatively assaying analytes.

BACKGROUND OF THE INVENTION

Analytical elements, especially multi-layer analytical elements for quantitative determination of various analytes of biological interest are known from U.S. Pat. Nos. 4,670,381; 4,517,288; 4,258,001; 4,066,403 and 3,992,158. Elements for assaying analytes such as carbon dioxide by enzymatic procedures, aspartate aminotransferase (AST), lactate dehydrogenates (LDH) and alanine aminotransferase (ALT) utilize NADH and measure reflectance density at 340 nm to obtain a quantitative determination of the analyte of interest.

In the case of the analytes just referred to, the measurement is made spectrophotometrically using a reflectometer. In a reflectometer, a beam of energy such as light is reflected off a mirror and subsequently through the support, reagent and registration layers of the element. The light is then reflected back through a filter onto a detector means such as a photodiode. The change in reflectance density ($D_R$) corresponds to the concentration of the analyte in a test solution. In a number of existing reflectometers the maximum obtainable $D_R$ is about 1.5 in the range 320 to 360 nm. The problem is that in some end point assays, such as the enzymatic approach to measuring $CO_2$, the maximum $D_R$ generated is about 2.0 at 340 nm. Obviously, using reflectometers with a maximum obtainable $D_R$ of 1.5 results in significant compression of the usable dynamic range for these assays, and therefore degraded precision.

SUMMARY OF THE INVENTION

Figure 1:
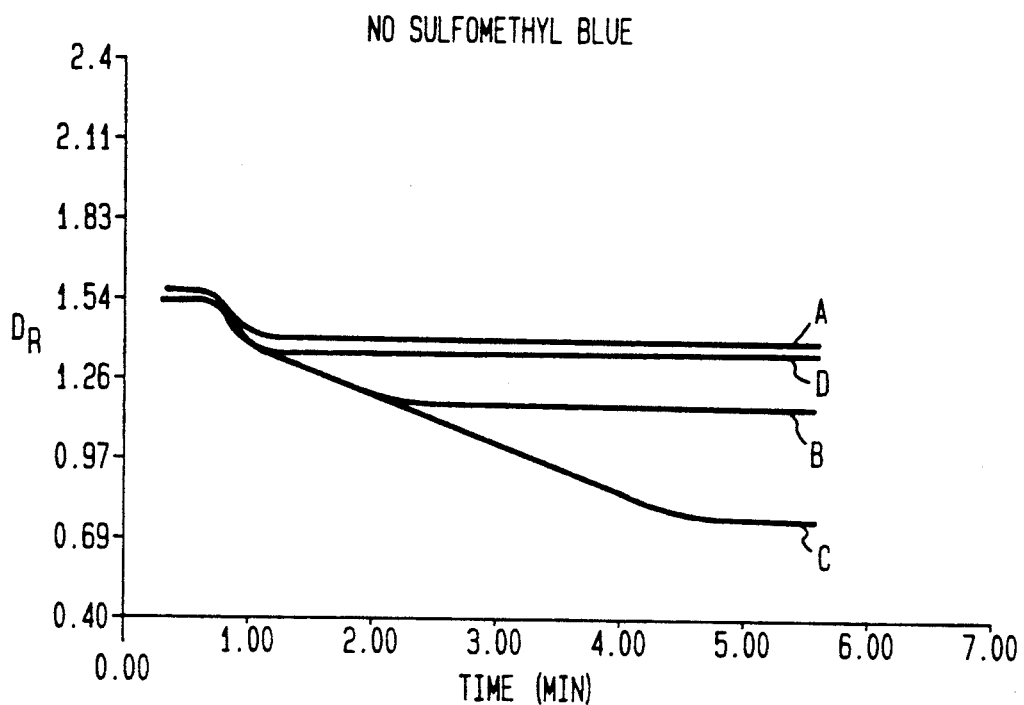
FIG. 1 shows the $D_R$ of an analytical element without a dye.

The present invention provides an analytical element for quantitatively assaying an analyte by measuring reflection density in the range 320 to 360 nm wherein said element comprises a reagent layer and a registration layer characterized in that one of such layers contains a dye with low absorptivity in the range 320 to 360 nm and high absorptivity in the range 640 to 720 nm.

The inclusion of the dye in the element increases the $D_R$ (reflectance density) dynamic range which leads to more precise analyte quantitative measurements in the range 320 to 340 nm. Finally, this invention obviates many of the instrument to instrument differences among reflectometers that influence 640 to 720 nm energy, as well as differences in 640 to 720 nm energy that occurs over time in the same machine, such as aging of the light source. This invention significantly increases the manufacturing latitude for existing reflectometer configurations. Filter cost can be reduced since less stringent requirements would be placed on the blocking characteristics of these filters.

DETAILS OF THE INVENTION

As stated hereinbefore, the maximum reflectance densities that can be measured at 340 nm in a number of existing reflectometers is about 1.5 $D_R$. A careful analysis of these reflectometers show that usually their light sources are rich in energy in the range 640 to 720 nm, the first harmonics of the range 320 to 360 nm. This light source is relatively poor in energy at 320 to 360 nm. In operation, energy from the light source is reflected off a mirror into the various layers of the analytical element. The element itself reflects energy which is rich at 640 to 720 nm and relatively poor at 320 to 360 nm. The energy reflected from the element passes through an interference filter which is designed to only allow energy at 320 to 360 nm to pass. However, some of the 640 to 720 nm energy passes through the filter. The energy passing through the interference filter then strikes a photodiode. The sensitivity profile of the photodiode shows that it is relatively insensitive at 320 to 340 nm and extremely sensitive to 640 to 720 nm. The result is that the 640 to 720 nm energy that manages to pass through the interference filter combines with the energy that passes through at 320 to 360 nm strikes the photodiode causing the reflectance density ($D_R$) to fall. Thus, in many cases, the maximum $D_R$ seen in, for example, a carbon dioxide end point assay is about 1.4. This means that the measurement of end point chemistries at 340 nm is often made on reflectometers with a compressed scale ranging from 0.6 to 1.4 $D_R$.

We have been able to identify a class of dyes which, when included in a layer of the analytical element, significantly reduces the 640 to 720 nm energy available to fall on the interference filter. The result is that significantly less 640 to 720 nm energy strikes the photodiode, thereby increasing the maximum density which the reflectometer can measure in the range 320 to 360 nm.

The class of dyes which are useful in this invention has the structure

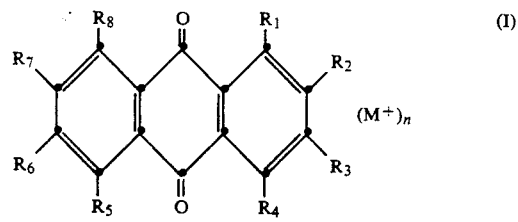

wherein $R_1$, $R_2$, $R_3$, $R_4$, $R_5$, $R_6$, $R_7$ and $R_8$ are each independently hydrogen, hydroxyl, sulfomethylamino, —NH(SO_3)$^-$ or sulfonic acid —$SO_3^-$ wherein at least two of $R_1$, $R_2$, $R_3$, $R_4$, $R_5$, $R_6$, $R_7$ and $R_8$ are —$SO_3^-$; $M^+$ is $Na^+$ or $K^+$ and n is at least 2. Such dyes are included in the relevant elements at a coverage of 0.1 to 0.4 g/m$^2$, although some dyes within the above structure will be effective at coverages outside of this range. Coverage is dictated by the amount of dye that gives sufficient $D_R$ across the range 640 to 720 nm without significantly contributing to increased $D_R$ across the range 320 to 360 nm. Especially useful dyes within the above structure include those in which n is up to 4. The useful dyes absorb energy at 680 nm and is relatively transparent at 340 nm. It is preferred that the dyes be water soluble for coating convenience, although water insoluble dyes can be used. A particularly useful dye has the structure

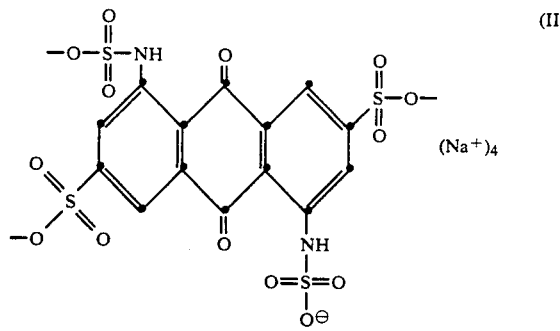

This dye is representative of the uniqueness of the useful dyes covered by structure I in that it has a relatively transparent band from 310 to 480 nm and a significant absorption band from 550 to 750 nm.

The dry multilayer test element provided by this invention comprises one or more reagent zones or layers and registration zones or layers. All reference hereinafter to layers also refers to zones. In one embodiment of the invention, the element comprises buffered reagent layer(s) and buffered registration layer(s). The layers of the element may be self-supporting, but are preferably on a support. The reagent layer is preferably permeable and porous. Permeability, including permeability arising from porosity, can be achieved through the presence of various carriers, matrices, or binders, such as fibrous materials or porous, non fibrous materials described in the above referenced U.S. Pat. No. 4,144,306. A preferred permeable binder of the invention is the above-described class of blushed polymers. Also useful as a porous carrier is a polymer binder with an inert particulate material, such as microcrystalline cellulose, dispersed therein. Pigment particles may be incorporated in the reagent layer for light reflecting purposes.

Registration layers are described in the above referenced U.S. Pat. No. 4,144,306. The registration layer is permeable to receive diffusible material from the reagent layer.

The preferred elements of the present invention include a spreading layer, a subbing layer, a reagent layer, a registration layer or a combination registration/reagent layer. The composition of these layers and their location in the element are known in the art and are described in U.S. Pat. No. 3,992,158 and the above referenced U.S. Pat. No. 4,144,306 are incorporated herein by reference. For example, spreading layers can be isotropically porous, achieving such porosity through the use of inert particle materials and/or blush polymers, and can be positioned adjacent to the reagent layer as the outermost layer of the element (if a multilayer element is used). Any of the layers of the present invention may also include well known addenda, such as buffers, surfactants, or coating aids, as described in the above-referenced U.S. Pat. No. 4,144,306.

Multilayer elements of the invention can be prepared by various laminating or coating techniques well-known in the art, such as hand-coating, blade coating, bead coating, or dip coating. The elements may be self supporting or carried on a support. Useful support materials include a variety of polymeric materials, such as cellulose acetate, poly(ethyleneterephthalate), polycarbonates, and polyvinyl compounds such as polystyrenes. The support is radiation transmissive. Coating and laminating techniques, along with support materials, are further described in the above-referenced U.S. Pat. No. 4,144,306.

For coatable reagent layers, a coating solution or dispersion including a binder and coated as discussed herein and dried to form a dimensionally stable zone. The thickness of any reagent layer and its degree of permeability are widely variable and depend on actual usage. Dry thicknesses of from about 10 to about 100 m$\mu$ are convenient, although more widely varying thicknesses can be used. Fibrous reagent layers can be formed by impregnation of a fibrous matrix, in accordance with well-known techniques.

Registration layers and other layers can be prepared using methods and thicknesses as used when preparing coatable reagent layers, but with constituents appropriate for the particular layer.

The elements of the invention are used by applying a sample of body fluid to be assayed to the element. Generally, the element will be formed so that the liquid first contacts one or more spreading layers or zones. After application of the liquid, the element may be exposed to any conditioning, such as heating or humidification, that is desirable to quicken or otherwise facilitate any test result.

After an appropriate time to allow for diffusion of the sample from the spreading layer to the reagent layer and the registration layer, the amount of detectable material in the registration zone is determined spectrophotometrically on a reflectometer.

EXAMPLE

To demonstrate the effectiveness of including a dye represented by structure I in an analytical element for making reflectometric measurements at 320 to 360 nm, the dye sulfomethyl blue having structure II was included in the reagent layer of the following element for assaying $CO_2$.

| $CO_2$ ANALYTICAL ELEMENT | Dry Amount Coverage (/m$^2$) | Range (/m$^2$) |
| --- | --- | --- |
| Spreading Layer | | |
| Barrium Sulfate | 108.595 g | 50–250 g |
| Cellulose Acetate | 8.629 g | 2.0–10.0 g |
| Triton X-405 Surfactant | 2.159 g | 0.5–5.0 g |
| Tris(hydroxymethyl)-aminomethane (THAM) | 1.385 g | 0.0–5.0 g |
| Tris hydrochloride (Tris HCl) | 1.203 g | 0.0–5.0 g |
| Estane Resin | 1.082 g | 1.0–5.0 g |
| Subbing Layer | 1.070 g | 0.3–5.0 g |
| N-vinylpyrrolidone (PVP) | | |
| Reagent Layer | | |
| Gelatin | 10.0 g | 1.0–20.0 g |
| Alkanol XC Surfactant | 0.1 g | 0.05–2.5 g |
| Zonyl FSN Surfactant | 0.02 g | 0.01–2.5 g |
| MgSO$_4$ | 0.50 g | 0.1–5.0 g |
| Tricine | 3.401 g | 0.5–5.0 g |
| Phosphoenolpyruvate | 3.25 g | 2.5–10.0 g |
| Phosphoenolpyruvate Carboxylase | 1524 U | 1,000–20,000 U |
| Registration Layer | | |
| Gelatin | 7.14 g | 1.0–20.0 g |
| Alkanol XC Surfactant | 0.1 g | 0.05–2.5 g |
| Zonyl FSN Surfactant | 0.020 g | 0.01–2.5 g |
| Bis(vinylsulfonyl-methyl)ether (BVSME) | 0.173 g | 0–2.5 g |
| Tricine | 3.401 g | 0.5–5.0 g |
| NADH | 3.0 g | 2.0–5.0 g |

| CO₂ ANALYTICAL ELEMENT -continued | | |
|---|---|---|
| | Dry Amount Coverage (/m²) | Range (/m²) |
| MDH | 1076 U | 1,000–30,000 U |

While the dye was included in the reagent layer, it could just as well have been included in the registration layer.

Values for $CO_2$ were determined on test samples with the above $CO_2$ element on an EKTACHEM Clinical Chemistry Analyzer (available from Eastman Kodak Company, Rochester, N.Y.). The element is also available from Eastman Kodak.

Figure 2:
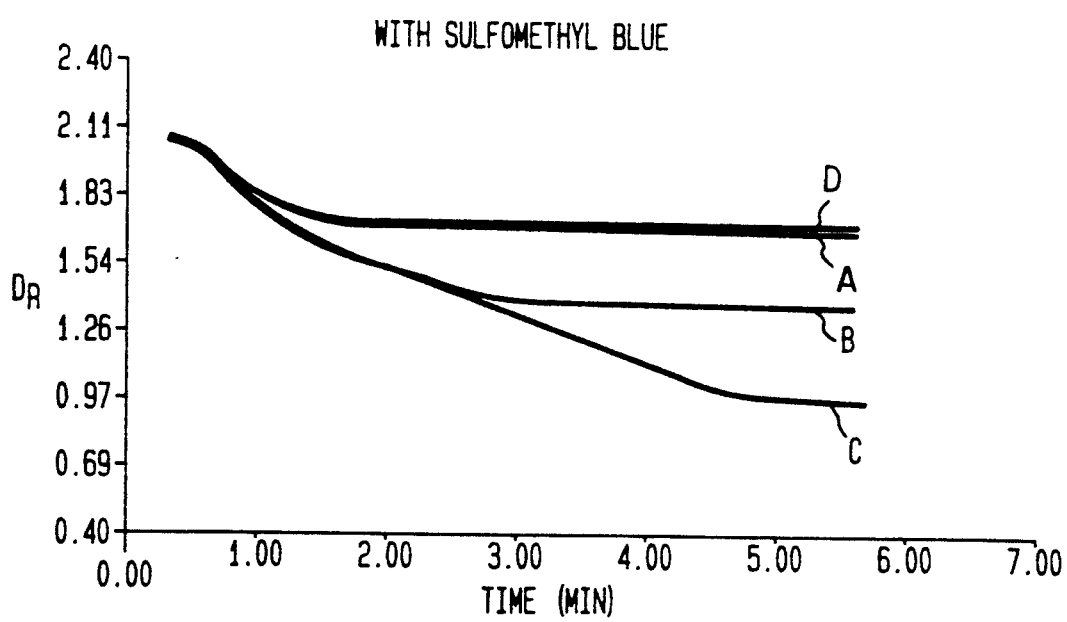
FIG. 2 shows $D_R$ over time for an analytical element with a dye.

Measurements of reflectance density ($D_R$) were taken using the above element without the dye (FIG. 1) and with the dye (FIG. 2). Readings were taken for test samples containing 0 mmol $CO_2$(A); 14.9 mmol $CO_2$ (B); 32.9 mmol $CO_2$ (C) and water containing no $CO_2$(D). Both FIGS. 1 and 2 describe a plot of reflection density against time. A comparison of these figures show that the addition of the dye to the element increases the $D_R$ at 340 nm for all of the curves (A), (B), (C) and (D).

Figure 3:
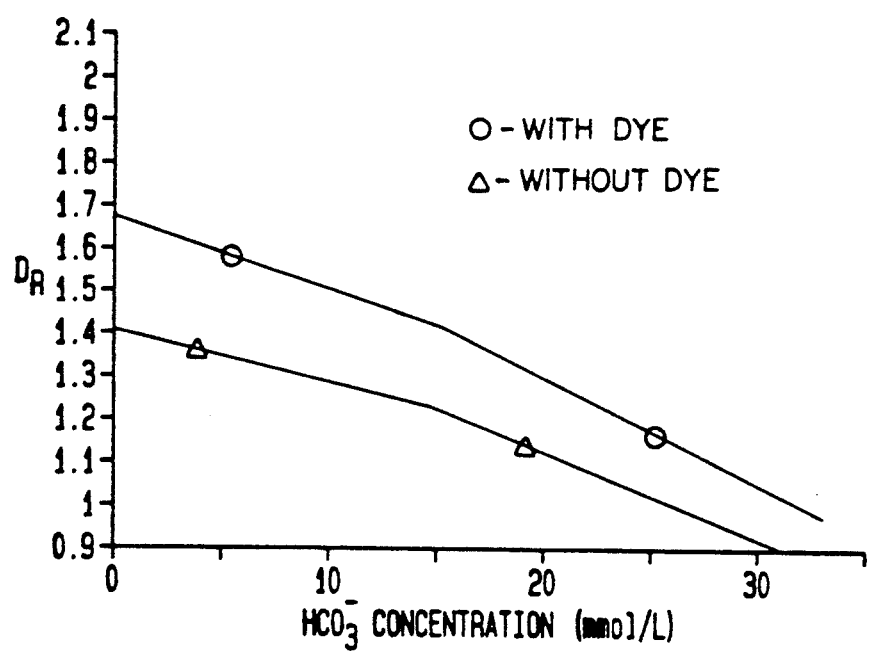
FIG. 3 shows $D_R$ as a function of analyte concentration for analytical elements with and without a dye used in the invention.

FIG. 3 is a plot of $D_R$ against concentration. FIG. 3 shows two curves for the $D_R$ of the test samples (A), (B), (C) and (D) measured in an element with (○) and without (Δ) the dye. The measurements were made at 340 nm. A comparison of the two curves shows that the $D_R$ decreases from about 1.4 to about 0.9 as the $CO_2$ concentration increases for the element without the dye. This is a change in $D_R$ of 0.5. For elements with the dye, the $D_R$ decreases from about 1.7 to about 1.0 units as of $CO_2$ concentration increases. This is a $D_R$ change of 0.7. This represents a 40 percent increase in the dynamic range which provides increased sensitivity at 340 nm.

The foregoing evidence demonstrates that the inclusion of a dye according to structure I in a dry analytical element increases the dynamic reflectance density range in which measurements of analytes can be made at 320 to 360 nm. The inclusion of the dye will also obviate reflectometer to reflectometer differences and differences within the same reflectometer over time.

While the present invention has been demonstrated with the use of an analytical element designed for measurement of carbon dioxide at 340 nm, it will be clear to those skilled in the art that any analyte measurement in the range 320 to 360 nm will be enhanced by the present invention.

The invention has been described in detail with particular reference to certain preferred embodiments thereof, but it will be understood that variations and modifications can be effected within the spirit and scope of the invention.

We claim:

1. An analytical element for quantitatively assaying an analyte by measuring reflection density in the range 320 to 360 nm wherein said element comprises a reagent layer and a registration layer wherein one of such layers contains a dye with low absorptivity in the range 320 to 360 nm and high absorptivity in the range 640 to 720 nm and has the structure

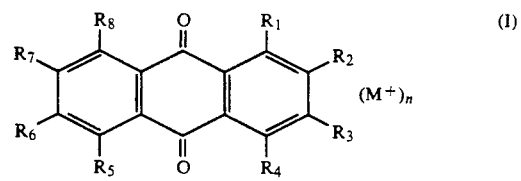

wherein:
$R_1$, $R_2$, $R_3$, $R_4$, $R_5$, $R_6$, $R_7$ and $R_8$ are each independently hydrogen, hydroxyl, —NH(SO₃)⁻ or —SO₃⁻ wherein up to 4 of $R_1$, $R_2$, $R_3$, $R_4$, $R_5$, $R_6$, $R_7$ and $R_8$ are —SO₃⁻; M⁺ is Na⁺ or K⁺ and n is 2 to 4.

2. The element of claim 1 wherein the dye is sulfomethyl blue having the structure

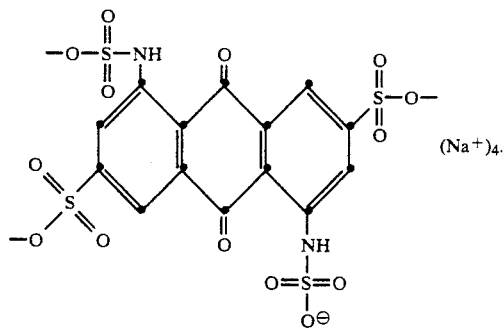

3. The element of claim 1 or 2 wherein the analyte is selected from the group consisting of carbon dioxide, aspartate aminotransferase, alanine aminotransferase and lactate dehydrogenase.

4. The element of claim 1 or 2 wherein the reflection density is in the range 320 to 360 nm.

5. The element of claim 3 wherein the dye is present in the element coated in the range 0.1 to 0.4 g/m².

6. The element of claim 1 or 2 wherein the dye is water soluble.

* * * * *